United States Patent [19]

Walch et al.

[11] 4,183,811
[45] Jan. 15, 1980

[54] MEMBRANE UNIT AND DEVICE FOR CLEANSING BLOOD

[75] Inventors: Axel Walch, Frankfurt; Ludwig Lammers, Idstein, both of Fed. Rep. of Germany

[73] Assignee: Hoechst Aktiengesellschaft, Frankfurt am Main, Fed. Rep. of Germany

[21] Appl. No.: 829,941

[22] Filed: Sep. 1, 1977

[30] Foreign Application Priority Data

Sep. 2, 1976 [DE] Fed. Rep. of Germany ....... 2639549
May 4, 1977 [DE] Fed. Rep. of Germany ....... 2719814

[51] Int. Cl.² ............................................ B01D 13/00
[52] U.S. Cl. .................................. 210/23 R; 210/24; 210/321 B; 210/493 M; 210/494 M; 210/500 M; 210/502
[58] Field of Search .......... 210/321, 493, 494, 500 M, 210/502, 22, 23

[56] References Cited

U.S. PATENT DOCUMENTS

| 3,367,504 | 2/1968 | Westmoreland | 210/321 R |
| 3,608,729 | 9/1971 | Haselden | 210/500 M |
| 3,827,562 | 8/1974 | Esmond | 210/321 R |
| 3,888,250 | 6/1975 | Hill | 210/494 M |
| 4,013,564 | 3/1977 | Nose | 210/321 R X |
| 4,045,352 | 8/1977 | Rembaum et al. | 210/500 M |
| 4,048,064 | 9/1977 | Clark | 210/500 M |

Primary Examiner—Charles N. Hart
Assistant Examiner—Ferris H. Lander
Attorney, Agent, or Firm—Schwartz, Jeffery, Schwaab, Mack, Blumenthal & Koch

[57] ABSTRACT

A membrane unit and apparatus for removing toxic metabolites and metabolites normally present in urine from blood is disclosed. The unit comprises a cavity through which the contaminated blood passes, said cavity comprising at least one permselective membrane and at least one adsorbent. The apparatus comprises at least one membrane unit which is connected to inlet and outlet means for transporting contaminated blood to the unit and decontaminated blood from the unit.

33 Claims, 5 Drawing Figures

MEMBRANE UNIT AND DEVICE FOR CLEANSING BLOOD

BACKGROUND OF THE INVENTION

1. Field of the Invention

The present invention relates to a membrane unit, an apparatus comprising a membrane unit and a method for decontaminating blood, by removing metabolite contaminates, i.e., toxic metabolites and metabolites normally present in urine.

2. Description of the Prior Art

Dialysis, diafiltration and hemoperfusion are known methods for removing toxic metabolites from blood. By metabolites are meant those components of the living cells which control the normal course of metabolic reactions, as well as products of metabolism formed or catabolized in human or animal organisms, such as urea, creatinine, peptides, carbohydrates and electrolytes, e.g., sodium or potassium salts. In dialysis and diafiltration separation is achieved by means of filtration via selectively permeable membranes hereinafter referred to as permselective membranes. Hemoperfusion is based on the principle of adsorption.

In the dialytic process the substances to be eliminated, namely water and substances normally present in urine, that is, uric acid, urea, creatinine, carbohydrates, electrolytes and peptides, are removed through a permselective membrane which exchanges the contaminants with a rinsing solution containing some of the substances which are vital to the organism. The exchange of diffusible substances across the permeable membrane is caused by the difference in concentrations on each side of the membrane.

The driving force in the diafiltration process is an adjustable pressure gradient. Any substance of a size below the porosity limit of the permselective membrane is pressed out as an ultrafiltrate in the same ratio of concentration as in blood. The ultrafiltrate may be rejected; however, a certain portion of the ultrafiltrate extracted from the blood must be returned to the bloodstream with all vital substances in a physiological ratio of concentration. Dialysis and diafiltration find primarily utility in treating persons suffering from chronic kidney diseases.

Conversely, hemoperfusion is based on a different principle of operation, and its application has up to now been almost exclusively limited to cases in which a paticularly rapid detoxification of the blood is required; as in acute failures of the liver or intoxications. In this method, adsorbents, such as activated carbon or macroporous resins are used to adsorb toxic metabolites. The adsorbents, which are usually enveloped by a porous membrane material, are generally used in granulated form, enclosed as micro-capsules in an aqueous suspension, coated upon support webs or used as fiber bundles disposed in columns through which contaminated blood passes. The enveloping of the adsorbents in a porous membrane material is preferred since it prevents direct contact with the blood which improves blood compatibility. Nevertheless, there is still a considerable risk of damaging the blood, particularly from loss of blood cells and proteins, from micro-embolisms due to washed-out adsorbent particles, and from an interruption of the steady flow in the column passed by the blood. In view of this high risk, the use of hemoperfusion is limited to cases in which the patient is comatose.

An additional disadvantage of the hemoperfusion systems is that the adsorbent is not adequately capable of adsorbing all metabolites normally present in urine, such as water, urea, electrolytes and ammonia. Even the use of additional complex and expensive measures, such as the inclusion of enzymes in micro-capsules, do not result in satisfactory removal of these metabolites.

It has heretofore been suggested to combine diafiltration and hemoperfusion by connecting corresponding devices in series in order to utilize the rapid detoxifying action of hemoperfusion and to extract the non-adsorbable metabolites normally present in urine. This procedure is, however, disadvantageous due to the high blood-filling and residual volume of the devices; in particular, the patient is exposed to the risk of hypotension. Moreover, in addition to the problems inherent in the use of the hemoperfusion device previously described, there is the danger of damaging the blood due to the use of additional, complex apparatus. Finally, it is difficult to coordinate the devices, and further their operation is extremely expensive.

It has also been proposed to pass the ultrafiltrate resulting from diafiltration over toxin-adsorbing substances and subsequently return the detoxified filtrate to the blood stream. The devices operating according to this procedure have, in particular, the disadvantage that only the ultrafiltrate which is separated from the blood, and not the bulk of the blood is contacted with the adsorbent. Thus, there remains a need in the art for a simple but efficient means of removing metabolite contaminants from blood that avoids the dangers and problems associated with the existing means.

SUMMARY OF THE INVENTION

Accordingly, it is an object of the present invention to provide a membrane unit for the simultaneous removal of toxic metabolites and metabolites normally present in urine from blood, which is only slightly affected by the disadvantages heretofore experienced in the art and which is characterized, in particular, by simplicity, reduced patient risk and rapid and complete removal of metabolites.

Another object of the invention is to provide an apparatus for the simultaneous removal of toxic metabolites and metabolites normally present in urine from blood.

Still another object of the invention is to provide a method for removing metabolite contaminants from blood.

The foregoing objects and advantages of the present invention are accomplished by providing a membrane unit which removes toxic metabolites and metabolites normally present in urine from blood comprising a cavity through which the contaminated blood passes which is formed by at least one permselective membrane and at least one adsorbent. The adsorbent is preferably enveloped by or embedded into a porous membrane.

The particular construction of the membrane unit varies, depending on its intended use. Generally, the permselective membrane is placed parallel and adjacent to the surface of the adsorbent which, preferably, has a profiled pattern. However, a structure in which the permselective membrane forms a capillary in which the adsorbent occupies the interior space of the capillary is also contemplated by the invention. When the unit is constructed with the permselective membrane and adsorbent parallel to each other, it may be rolled spirally or folded to form an accordian structure in which the adsorbing layer is disposed between the adjacent permselective membrane layers and vice versa.

The membrane unit of the present invention may be incorporated into an apparatus for removing toxic metabolites and metabolites normally present in urine from blood by linking it to at least one inlet and outlet means for transporting blood to and from the unit. Alternatively, this apparatus may be formed by linking a plurality of membrane units in series.

The membrane unit and apparatus derived therefrom thus provide a simple and efficient method for simultaneously removing toxic metabolites and metabolites normally present in urine from blood by passing contaminated blood through the membrane unit and collecting the decontaminated blood from the apparatus.

Other objects and advantages of the present invention will be evident to those of skill in the art after studying the complete disclosure and the accompanying drawings.

BRIEF DESCRIPTION OF THE DRAWINGS

Several embodiments of the invention are explained in detail by reference to the accompanying drawings of which

DETAILED DESCRIPTION OF THE PREFERRED EMBODIMENTS

The permselective membrane of the present invention is suited for removing metabolites normally contained in urine, such as water, electrolytes, urea, and ammonia, and is composed of materials which are conventionally used in dialysis and diafiltration, for example, regenerated cellulose, cellulose ester, cellulose ether, carbohydrate gels, polypeptides, proteins, polyamides, polysulfones, block copolymers with polycarbonate, polymers or copolymers from derivatives of acrylic or methacrylic acid, such as nitriles or esters, and polymers or copolymers of vinyl alcohol. To facilitate storage, so-called "dry membranes" may be employed, which are redampened prior to use. The size of the pores of the permselective membrane is in the range of about 2 to 10 nm. Optionally, the membrane may be provided with an antithrombogenic and biocompatible finish.

According to the most preferred embodiment, the permselective membrane is applied to a carrier which is capable of absorbing and/or carrying off the filtrate (e.g., water, electrolysis, ammonia, urea) or a rinsing solution which performs the same function. The carrier also serves to reinforce and support the membrane which facilitates handling by reducing the risk of damage to the membrane. The carrier may be made of paper, a woven fabric, a non-woven, a fibre fleece or a mesh net of a synthetic material. Plates or films having a liquid-conducting profile or made of a porous or absorbent material are also suitable carriers. Exemplary of such carriers are sintered polyethylene or absorbent artificial sponges, preferably composed of regenerated cellulose, commonly known as sponge cloth material.

The production of artificial sponge from regenerated cellulose is known to those of skill in the art. Cellulose is first converted into viscose. Reinforcing fiber, such as cotton fiber having a length of 12 to 15 millimeters, may be worked into the viscose, and to enhance pore formation grains of salt, particularly glauber's salt crystals of an appropriate grain size may be included. The composition is then applied to an endless carrier web and precipitated under the influence of heat by a coagulating agent, for example, by a water bath of approximately 100° C. In the water bath a large portion of the salt is dissolved and washed out. Subsequently, the artificial sponge passes a precipitating bath containing aqueous sulphuric acid, a chlorite bleaching bath, if necessary, and an additional washing line, where it is thoroughly washed in water. Finally, the absorbed water is squeezed out and the sponge is dried.

The chemical purity of the artificial sponge must meet strict requirements, comparable to the standards specified for aseptic gauze and gauze bandages made of cellulose. It must not contain toxic compounds or impurities. Thus, the final washing in water during manufacture of the artificial sponge must be thorough, and accordingly, it is preferred to use salt-free water. The addition of dyes or optical brighteners should also be avoided, when the artificial sponge is intended for this particular purpose. In order to reduce clouding of the aqueous extract a cellulose ether is cross-linked on the surface of the artificial sponge and is mixed with a wetting agent to produce hydrophilic properties.

The permselective membrane may be loosely arranged on the carrier or fixed to it by bonding or sealing. Preferably the membrane layer is formed directly on the surface of the carrier by coagulation or regeneration of a suitable solution of the membrane-forming substance.

The primary function of the adsorbent is to bind toxic metabolites. As contemplated by the invention, the adsorbent comprises sheet-like or fibrous bodies as well as granules and powders. The sheet-like or fibrous bodies generally exist as woven, knitted, non-woven or braided fabrics which, optionally, may be enveloped by another membrane. By "woven fabric" is meant a sheet-like body composed of warp and weft while the term "braided fabric" denotes a body similar in structure to a normal wire mesh. The enveloping membrane is selectively permeable and has pores ranging from about 2 to 100 nm. It may be made of the same materials as the permselective membrane and thus may have the same structure and characteristics as the permselective membrane. In order to differentiate this membrane from the permselective membrane, it is hereinafter referred to as the "porous membrane".

When a granulated or powdery adsorbent is used, it is preferably embedded in the porous membrane, although it may also be applied to the surface of a sheet-like body without the need for a porous membrane.

The adsorbents of the invention are thus sheet-like, fibrous, granular or powder forms of activated carbon, compounds having ion exchange capacities, such as sulfonated or quaternated polystyrene or carbohydrates (e.g., cellulose or sepharose), hydrophobic plastics or synthetic resins, such as porous polystyrene resin or polyethylene fabric. Preferably, the activated carbon is in the form of a woven, knitted, non-woven or braided fabric or a fiber consisting of a textile material which has been pyrolized in the absence of oxygen and activated into carbon and which may be enveloped by the porous membrane. In this preferred embodiment the textile material is composed of fibers or synthetic materials such as polyamides, polyester or polyacrylonitrile, or of natural materials such as cellulose.

The porous membrane is used to prevent direct contact between the blood and the adsorbent in situations where direct contact is not desirable. In such cases, the porous membrane is preferably generated directly on the surface of the adsorbent or is prepared by pouring, regenerating or coagulating a solution of the membrane-forming polymer and the granulated adsorbent. It may additionally be provided with an anti-thrombogenic and biocompatible finish.

According to another preferred embodiment of the invention, the adsorbent and the membrane enveloping the adsorbent if present are provided with a profile on the surface facing the permselective membrane, which maintains the cavity through which the blood passes in lieu of a spacer. Alternatively, a carrier having a profiled surface upon which the permselective membrane is applied may be used. Without such a profile, a spacer must be disposed between the permselective membrane and the adsorbent to form the required cavity. Supporting plates and woven or braided fabrics may be employed as spacers.

The surface profile is formed by regularly distributed burls or streaks or by a corrugation, covering the entire surface of the porous membrane and possibly the permselective membrane or carrier. The profile not only maintains the cavity required for the passage of the blood, but also causes good mixing of the contaminated blood and enlarges the surface area of the adsorbent and in some cases the permselective membrane.

In another embodiment of the invention the above-described membrane unit is equipped with an additional permselective membrane extending adjacent to the back of the adsorbent. The "back of the adsorbent" is that surface of the adsorbent or of the porous membrane covering the adsorbent, which does not face the surface of the first permselective membrane. A second cavity is formed by the second permselective membrane and the back of the adsorbent, through which the contaminated blood passes. The direction of flow is usually the same as in the original cavity, so that the blood passes the cavities in parallel direction. However, the blood may also pass the second cavity in opposite direction. In this case, deflecting elements are required to introduce the blood into the second cavity after passing through the first.

In the three-component membrane unit the permselective membranes are made of either the same or different material. Thus, the unit may comprise permselective membranes having different volumetric flows and different molecular weight exclusion limits. Preferably, the permselective membranes are applied to carriers.

According to another embodiment of the invention, an apparatus for the simultaneous removal of toxic metabolites and metabolites normally contained in urine from blood is provided. This apparatus comprises at least one inlet for the contaminated blood and at least one outlet for the decontaminated blood. Both the inlet and outlet means are connected to a cavity having at least one membrane unit constructed in accordance with the invention. If a permselective membrane applied to a carrier made of a porous or absorbent material, such as, an artificial sponge, preferably composed of regenerated cellulose, is used it may be possible to omit an element for draining off the filtrate. However, in such cases it is mandatory that the apparatus be of sufficient dimensions so as to be readily adapted to the flow and pressure ratios which vary with the absorption of filtrate. In such cases, draining of the non-adsorbable substances is substantially reduced, and primarily water and adsorbable toxic metabolites are extracted. Conversely, if one or more outlets are provided for the filtrate or the rinsing solution, they are connected with the permselective membrane and possibly a fluid-conducting carrier.

Figure 1:
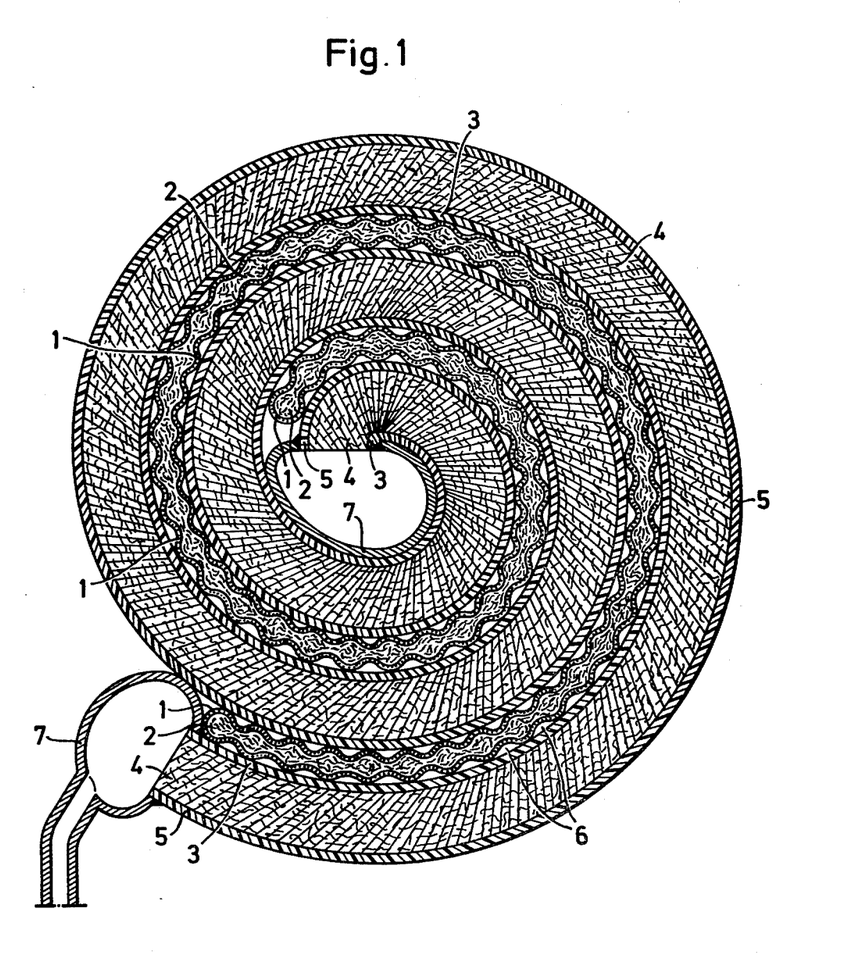
FIG. 1 is a sectional view of a spirally rolled membrane unit.

Various embodiments of the invention are illustrated by the drawings. FIG. 1 represents a sectional view of a spirally rolled membrane unit. It comprises a porous membrane 1 enveloping the adsorbent 2 which due to its profiled surface is separated from the permselective membrane 3. The permselective membrane 3 is applied to a carrier 4 capable of absorbing and carrying off the filtrate which is also provided with a permselective membrane 5 on its opposite surface. Blood is introduced vertically to the plane of the drawing via an inlet, not shown. It enters the cavities 6 formed by the adsorbent 2 and the permselective membrane 3 or 5, respectively, passes the cavities and is subsequently drawn off from the device via an outlet, not shown. The filtrate penetrating the permselective membrane 3 or 5 or the rinsing solution is carried off via the carrier 4 which is connected with drain pipes 7. When the carrier is composed of an absorbent material, it may be possible to leave the filtrate in the carrier. Thus, the drain pipes 7 may be omitted. The blood passes the rolled membrane unit in axial direction, although it may also flow in the direction in which the spiral is rolled, in which case it is extracted either centrally or at the circumference of the rolled spiral, depending upon the direction of flow.

Figure 2:
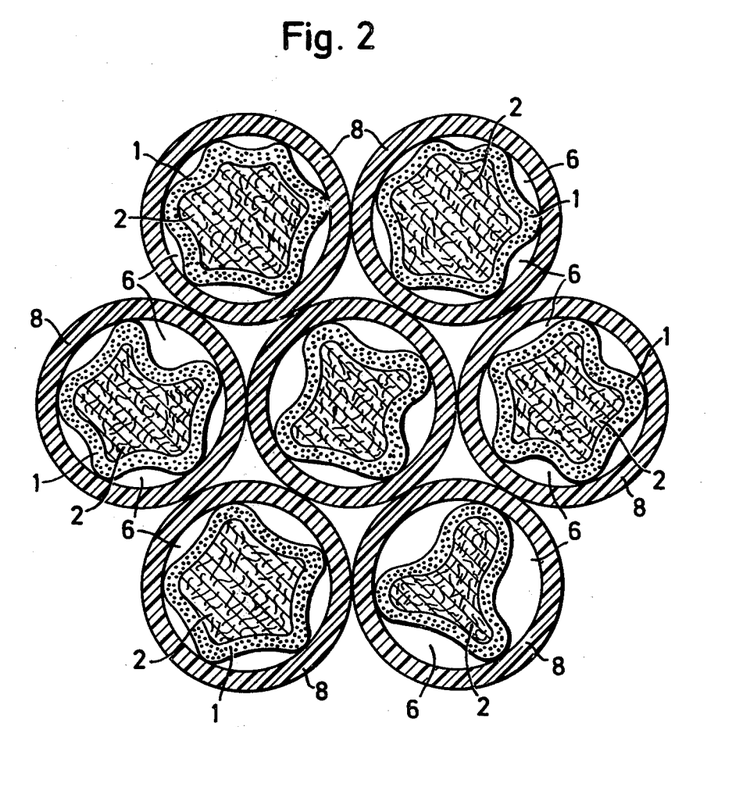
FIG. 2 is a sectional view of another embodiment of the membrane unit.

A further embodiment of the membrane unit shown in a sectional view in FIG. 2 comprises a plurality of capillary permselective membranes 8 of substantially equal length and diameter which are gathered up into a bundle and which at their ends, not shown, are anchored in a plate by embedding the ends in s synthetic resin. A granulated or fibrous adsorbent 2 covered by a porous membrane 1 is disposed in the interior space formed by each capillary membrane. When the contaminated blood is led through the interior space 6 of the capillary membrane or membranes 8, metabolite contaminants diffuse partly through the permselective membrane 8 and partly through the porous membrane 1 into the adsorbent 2 and are thus removed. It is also possible to modify the embodiment shown by separating the capillary permselective membranes 8 from one another, so that they are not in contact. As a result, the contacting area between the outside surface of the permselective membrane and the rinsing solution is increased.

Figure 3:
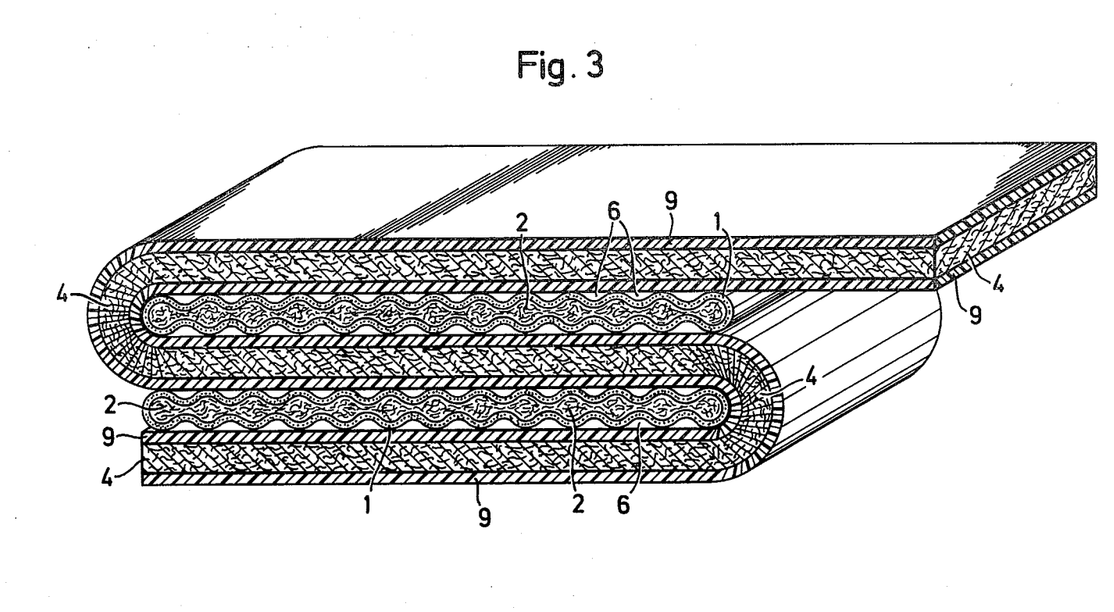
FIG. 3 is a sectional view in perspective of a third embodiment of the membrane unit in which the unit is folded into an accordian structure.

The embodiment of the membrane unit shown in a cross-sectional view in FIG. 3 comprises a carrier 4 capable of absorbing and carrying off the filtrate which is folded to form an accordian arrangement and is coated on either side with permselective membranes 9. Between adjacent layers of this fold-out arrangement, adsorbing layers 2 enveloped by a porous membrane 1 are situated which have profiled surfaces and thus form the channels 6. By interchanging the layers it is also possible to design a membrane unit in which the adsorbing layer covered by the porous membrane is folded to form an accordian arrangement while the carriers coated with permselective membranes on either side are placed between the neighboring layers of the fold-out arrangement.

Figure 4:
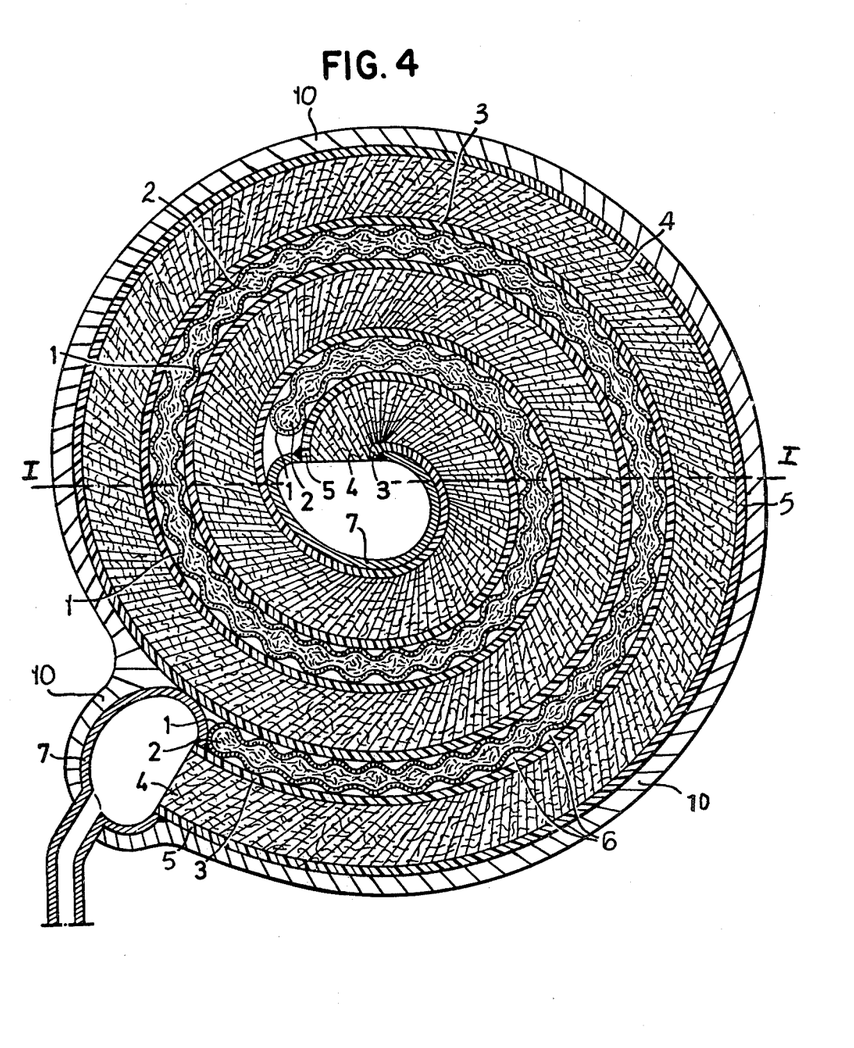
FIG. 4 is a sectional view of the membrane unit shown in FIG. 1, incorporated in the apparatus according to the invention.
Figure 5:
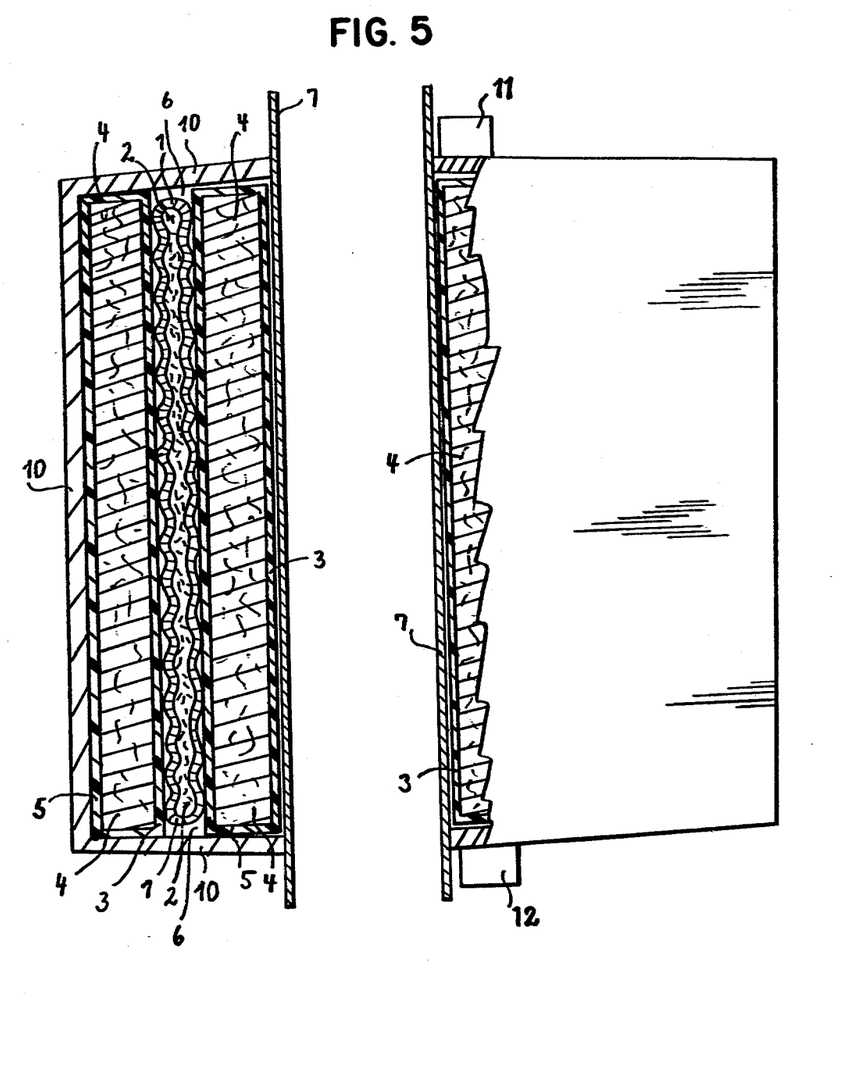
FIG. 5 is a front view, partly in section, of part of the apparatus, along line I—I of FIG. 4.

The apparatus shown in FIGS. 4 and 5 comprises a shell 10, provided with an inlet 11 for the contaminated blood and an outlet 12 for the decontaminated blood. Reference numerals 1 to 7 correspond to the reference numerals given in FIG. 1.

For reasons of clarity the membrane units depicted in FIGS. 1 to 5, the drain pipe 7, the inlet 11 and the outlet 12 are not shown true to scale, as far as thicknesses and lengths are concerned. In practice, usually adsorbent and carrier layers are used which are each about 0.5 to 3 millimeters thick. Thus, a plurality (50 to 100) of the alternating adsorbent and carrier layers shown may be incorporated in the apparatus.

Apart from the embodiments of the membrane unit shown in the figures, it is also possible to use membrane units comprising a pile of rectangular or circular plates arranged in series. In this case, a number of feed-in webs corresponding to the number of membrane units are provided for feeding the contaminated blood into the individual membrane units, and, similarly, a corresponding number of draining channels are placed at the opposite ends of the individual membrane units. However, the contaminated blood may also be fed into the first membrane unit in the pile and drawn off from the last membrane unit in the pile. In this embodiment, the blood is deflected at the end of each membrane unit and introduced into the neighboring unit passing in the opposite direction.

The membrane unit and the devices equipped with this unit which are the subject of the present invention are excellently suited for the simultaneous removal of toxic metabolites and metabolites normally present in urine from blood. The devices have a reduced volume and combine the advantages of dialysis and diafiltration devices with the advantages of the hemoperfusion device in that they are capable of separating water, urea, electrolytes and ammonia and also toxic metabolites from blood.

The membrane unit and purification apparatus thus provide an improved method for the simultaneous removal of toxic metabolites and of metabolites normally present in urine from blood. This method comprises subjecting metabolite contaminated blood simultaneously to a permselective membrane and an adsorbent which together form a cavity permeable to blood. The blood is passed through the cavity at excess or reduced pressure ranging from 0.1 to 1 bar. An ultrafiltrate results as in diafiltration. The filtrate may be absorbed by a carrier or drawn off. The substances extracted from the blood which are essential for the survival of the organism must be added in physiological concentration by means of a replacement liquid. However, the need for a replacement liquid and draining procedure may be eliminated by allowing the filtrate to be absorbed by the carrier, which simultaneously reduces the amount of non-adsorbable substances so that primarily water and adsorbable toxic metabolites are extracted. On the other hand, if the principle of dialysis is used a rinsing solution containing the substances vital to the organism must be passed over that surface of the permselective membrane which does not face the blood allowing the vital substances to diffuse across the permselective membrane into the blood.

While the invention has been described in terms of various preferred embodiments the skilled artisan will appreciate that various modifications, substitutions, omissions, and changes may be made without departing from the spirit thereof.

What is claimed is:

1. A membrane unit for simultaneously removing toxic metabolites and metabolites normally present in urine from blood, comprising at least one cavity through which the contaminated blood passes, said cavity being defined by a first wall comprised of a permselective membrane having a pore size adapted to selectively remove from the blood metabolites normally present in urine, including water, electrolytes, urea and ammonia, and a second wall spaced from said first wall and comprising at least one adsorbant for removing toxic metabolites from the blood, whereby the blood simultaneously directly contacts both said first and second walls in said cavity.

2. A membrane unit as defined by claim 1, wherein said adsorbent is enveloped by or embedded in a porous membrane.

3. A membrane unit as defined in claim 2, wherein the pore size of said porous membrane is larger than the pore size of said permselective membrane.

4. A membrane unit as defined by claim 1, wherein said permselective membrane is applied to a fluid-absorbing and/or fluid-draining carrier.

5. A membrane unit as defined by claim 4, wherein said carrier is an adsorbent material comprising a porous artificial sponge composed of regenerated cellulose.

6. A membrane unit as defined by claim 1, wherein said permselective membrane is applied to a carrier containing a rinsing solution.

7. A membrane unit as defined by claim 1, wherein the surface of the adsorbent facing away from the permselective membrane forms at least one other cavity through which the contaminatd blood passes, said cavity being formed by the surface of the adsorbent facing away from the permselective membrane and an additional permselective membrane.

8. A membrane unit as defined by claim 1, wherein said adsorbent comprises a pyrolized and activated sheet-like textile.

9. A membrane unit as defined by claim 8, wherein said textile is composed of fibers selected from the group consisting of polyamide, polyester, polyacrylonitrile and cellulose containing fibers.

10. A membrane unit as defined by claim 8, wherein said textile comprises activated carbon.

11. A membrane unit as defined by claim 1, wherein said adsorbent has an ion exchange capacity.

12. A membrane unit as defined by claim 1, wherein said adsorbent is selected from the group consisting of hydrophobic synthetic material and porous synthetic resin.

13. A membrane unit as defined by claim 1, wherein said adsorbent is a sheet-like body having a profiled surface.

14. A membrane unit as defined by claim 13, wherein the permselective membrane is applied to a fluid-absorbing and/or fluid-draining carrier and is folded to form an accordian structure wherein said adsorbent is disposed between adjacent layers of said structure.

15. A membrane unit as defined by claim 13, wherein said adsorbent is folded to form an accordian structure wherein the permselective membrane is applied to a fluid-absorbing carrier which is disposed between adjacent layers of said structure.

16. A membrane unit as defined by claim 1, wherein the permselective membrane comprises a hollow capillary structure in which the adsorbent is located in the hollow interior space of the capillary, whereby said cavity is defined between the adsorbent and the interior walls of said capillary structure.

17. A membrane unit as defined by claim 1, wherein said unit is spirally rolled.

18. An apparatus for purifying blood, comprising said membrane unit as defined by claim 1 and connected thereto at least one inlet means for admitting contaminated blood and at least one outlet means for releasing the decontaminated blood.

19. An apparatus as defined by claim 18, wherein said membrane unit is spirally rolled.

20. An apparatus as defined by claim 18, wherein said membrane unit is folded to form an accordian structure.

21. An apparatus as defined by claim 18, wherein said membrane unit contains absorbent carriers which retain and collect and/or drain the filtrate from said membrane unit.

22. An apparatus as defined by claim 21, wherein said absorbent carriers are artificial sponge composed of regenerated cellulose.

23. An apparatus as defined by claim 18, containing a plurality of membrane units arranged side by side to form alternating layers of permselective membranes, cavities and adsorbents.

24. An apparatus as defined by claim 23, wherein said membrane units are capillary membrane units wherein the permselective membrane comprises a hollow capillary structure in which the adsorbent is located in the hollow interior space of the capillary, whereby said cavity is defined between the adsorbent and the interior walls of said capillary structure.

25. A membrane unit as defined by claim 1, wherein a spacer is disposed between the at least one permselective membrane and the at least one adsorbent to form the required cavity.

26. A membrane unit as defined by claim 25, wherein the permselective membrane and adsorbent surfaces are approximately parallel.

27. A membrane unit as defined by claim 1, wherein the pore size of said permselective membrane is between about 2 and 10 nm.

28. A method as defined by claim 1, wherein said adsorbent is granulated or powdery and is applied to the surface of a sheet-like body to define said second wall.

29. A method for simultaneously removing toxic metabolites and metabolites normally present in urine from blood, comprising the step of simultaneously directly contacting the blood with at least one permselective membrane having a pore size adapted to selectively remove from the blood metabolites normally present in urine, including water, electrolytes, urea and ammonia, and at least one adsorbent for removing toxic metabolites from the blood.

30. A method as defined by claim 29, wherein said adsorbent is enveloped by or embedded in a porous membrane having a pore size larger than the pore size of said permselective membrane.

31. A method as defined by claim 29, wherein said permselective membrane is applied to a fluid-absorbing and/or fluid-draining carrier.

32. A method as defined by claim 31, wherein said carrier is an absorbent material comprising a porous artificial sponge composed of regenerated cellulose.

33. A method as defined by claim 29, wherein said adsorbent is a sheet-like body having a profiled surface.

* * * * *

UNITED STATES PATENT OFFICE
CERTIFICATE OF CORRECTION

Patent No. 4,183,811  Dated January 15, 1980

Inventor(s) Axel WALCH and Ludwig Lammers

It is certified that error appears in the above-identified patent and that said Letters Patent are hereby corrected as shown below:

In Column 3, line 60, kindly delete "electrolysis" and insert instead -- electrolytes --.

In Column 5, line 26, kindly delete "absorbent" and insert instead -- adsorbent --.

In Column 6, line 43, kindly delete "in s synthetic resin" and insert instead -- in a synthetic resin --.

In Column 7, line 60, kindly delete "simultaneously" and insert instead -- substantially --.

Signed and Sealed this

First Day of July 1980

[SEAL]

Attest:

Attesting Officer

SIDNEY A. DIAMOND
Commissioner of Patents and Trademarks